United States Patent [19]

Baxter

[11] Patent Number: 4,974,460
[45] Date of Patent: Dec. 4, 1990

[54] PRECISION LOCATING AND SUPPORTING DEVICE

[76] Inventor: James A. Baxter, 73a Friern Barnet Lane, London N20 OXT, United Kingdom

[21] Appl. No.: 249,138

[22] Filed: Sep. 26, 1988

[30] Foreign Application Priority Data

Sep. 25, 1987 [GB] United Kingdom ............... 8722634
Sep. 23, 1988 [GB] United Kingdom ............... 8822433

[51] Int. Cl.⁵ .................. G01N 35/04; G01N 35/06
[52] U.S. Cl. .................................. 73/864.91; 422/102
[58] Field of Search ................... 73/864.91; 422/102

[56] References Cited

U.S. PATENT DOCUMENTS

| | | | |
|---|---|---|---|
| 3,027,799 | 4/1962 | Weichselbaum . | |
| 3,615,239 | 10/1971 | Jones et al. | 141/130 X |
| 3,807,955 | 4/1974 | Note, Jr. et al. | 220/97 C X |
| 3,916,157 | 10/1975 | Roulette et al. | 73/53 X |
| 3,938,735 | 2/1976 | Wright et al. . | |
| 3,991,627 | 11/1976 | Laird et al. | 73/864.91 X |
| 4,000,976 | 1/1977 | Kramer et al. | 141/130 X |
| 4,039,288 | 8/1977 | Moran | 141/130 X |
| 4,094,641 | 6/1978 | Friswell | 215/12 R X |
| 4,096,965 | 6/1978 | Lessnig et al. | 73/864.91 X |
| 4,208,484 | 6/1980 | Sogi et al. | 435/286 |
| 4,256,697 | 3/1981 | Baldwin | 422/102 X |
| 4,278,437 | 7/1981 | Haggar | 422/102 X |
| 4,517,851 | 5/1985 | Tice | 73/864.91 |
| 4,518,076 | 5/1985 | Feisel et al. | 73/864.91 X |
| 4,738,827 | 4/1988 | Pierotti | 73/864.91 X |
| 4,797,257 | 1/1989 | Shaw | 73/864.91 X |

Primary Examiner—Tom Noland
Attorney, Agent, or Firm—Diller, Ramik & Wight

[57] ABSTRACT

Device serving for accommodating a small outer diameter vial in a larger diameter opening of a variety of different autosamplers and which controls the depth of insertion of an autosampler extraction element. The device comprises a sleeve having a body defined by an exterior surface of the sleeve, for accurately fitting the sleeve in a large diameter opening of an autosampler, and by an interior surface of the sleeve, for accurately fitting therein a small outer diameter vial, whereby an otherwise incompatible small outer diameter vial and larger diameter opening autosampler are rendered compatible.

4 Claims, 2 Drawing Sheets

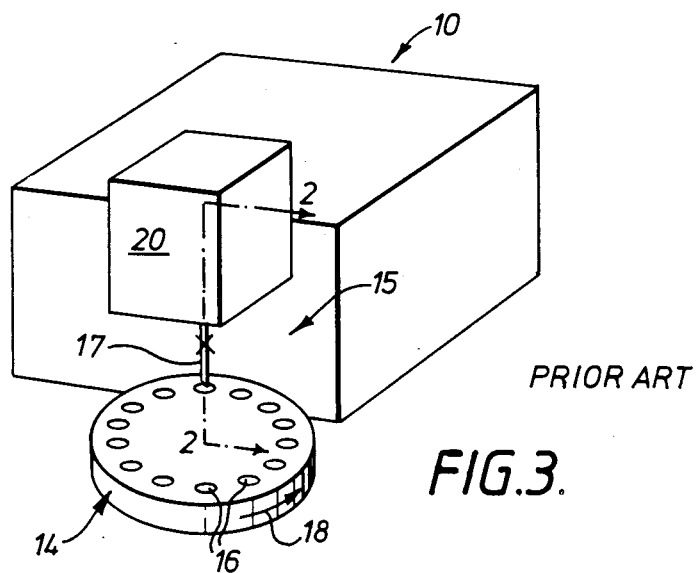
PRIOR ART
FIG.3.
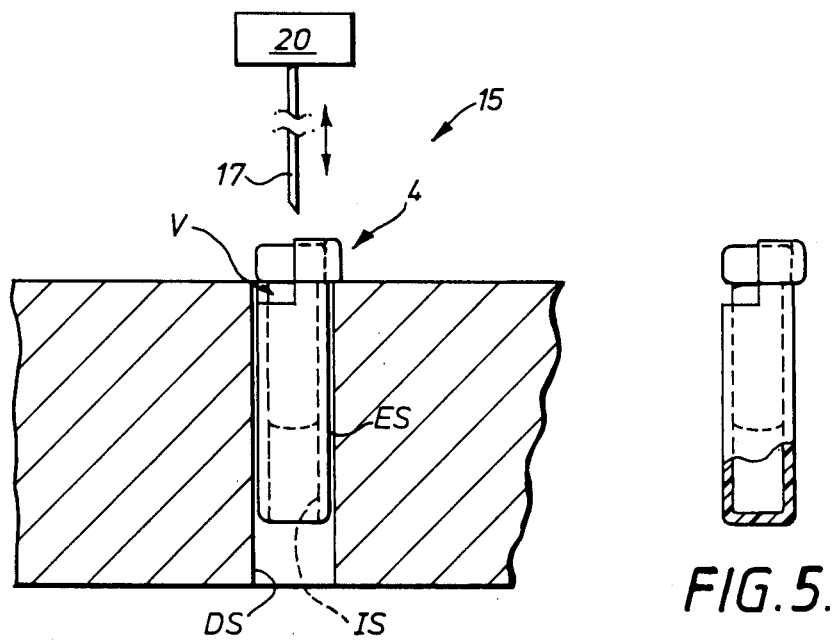
FIG.4.
FIG.5.

PRECISION LOCATING AND SUPPORTING DEVICE

FIELD OF THE INVENTION

The present invention relates to locating and supporting sleeve devices for vials, and in particular to devices of a certain shape and size for locating and supporting vials in analytical instruments, for example autosamplers used in Gas (GC) and Liquid (LC) Chromatography.

DESCRIPTION OF THE RELATED ART

In the analytical sciences it has become increasingly commonplace to use instruments with automatic sampling facilities (autosamplers), e.g. with chromatographs or spectrophotometers. Such facilities usually take the form of a carousel arrangement in which vials containing samples for examination are located around the periphery of the carousel. Thus samples may be separately presented for analysis on rotation of the carousel.

A known disadvantage of such autosamplers is that it is not normally possible for a needle, probe or other extraction device to remove all of the sample from any given vial in the sampler. In some instances, due to the size of the gap between the bottom of the vial and the extraction device, the amount of available sample is simply too small for withdrawal.

In cases where an adequate volume of sample is available the existence of a gap between the bottom of the vial and the extraction device presents no problem, but many laboratories, especially those in hospitals, frequently have to accept inadequate sample volumes for examination, and difficulties may then arise.

In particular chromatographic auto-samplers produced by Hewlett-Packard Company of 3000 Hanover Street, Palo Alto, California 94304, U.S.A. present particular problems as standard vials used by their GC autosampler model 7673A, must be positioned by a robotic arm, whilst the standard vials of their high performance (HP) LC model 1090A must remain immovable in a cartridge during sample extraction.

Thus, there is a clear need to provide a low volume vial which is sufficiently narrow to cause displacement of the sample contents when an extraction device enters the vial, enabling small quantities to be extracted from small sample volumes. Preferably, the vial also has an external convex-shaped bottom.

Unfortunately, vials meeting these requirements have been found to be too narrow to fit into typical autosampler devices of Hewlett-Packard.

SUMMARY OF THE INVENTION

Thus, the present invention provides a precision locating and supporting device for a vial which enables the user to fit the vial accurately into autosamplers produced by Hewlett-Packard for GC and HPLC.

More specifically the present invention provides a precision locating and supporting device for accommodating a small outer diameter vial in the larger diameter openings of a variety of different autosamplers and which controls the depth of insertion of the autosampler extraction means comprising a sleeve, means defined by an exterior surface of said sleeve for accurately fitting the sleeve in a large diameter opening of an autosampler, and means defined by an interior surface of said sleeve for accurately fitting therein a small outer diameter vial whereby an otherwise incompatible small outer diameter vial and larger diameter opening autosampler are rendered compatible.

In particular the interior surface of the cylindrical sleeve device may be an axial bore where the ratio of the height of the sleeve to outside diameter is in the range of 1.5 to 4.5, and the ratio of the outside diameter to the inside diameter is in the range of 1.5 to 2.75.

The present invention also provides a combination of the precision locating and supporting device with a fitted vial.

The present invention further provides a combination of an autosampler and a precision vial locating and supporting device as described above comprising an autosampler having a plurality of large diameter openings for receiving in each a small outer diameter vial, said precision vial locating and supporting device comprising a sleeve, said sleeve having means defined by an exterior surface for accurately matching the large diameter openings of said autosampler, said sleeve being accurately fitted in one of said autosampler openings, means defined by an interior surface of said sleeve for accurately matching a small outer diameter vial, and a smaller outer diameter vial accurately fitted in said sleeve interior surface whereby an otherwise incompatible small outer diameter vial and larger diameter opening autosampler are rendered compatible.

In addition the present invention provides a method for accommodating a small outer diameter vial in the larger diameter openings of a variety of different autosamplers and controlling the depth of insertion of the autosampler extraction means by locating and supporting the vial in a device according to the present invention.

BRIEF DESCRIPTION OF THE DRAWING

One embodiment of a precision and supporting device according to the invention will now be described by way of example, with reference to the accompanying diagrammatic drawing in which:

FIG. 3 is a highly diagrammatic perspective view of a conventional autosampler.

FIG. 4 is an enlarged fragmentary view of the device of the invention associated with a carrier of the autosampler.

FIG. 5 is a fragmentary side elevational view of another device of the invention.

DESCRIPTION OF THE PREFERRED EMBODIMENT

Figure 1:
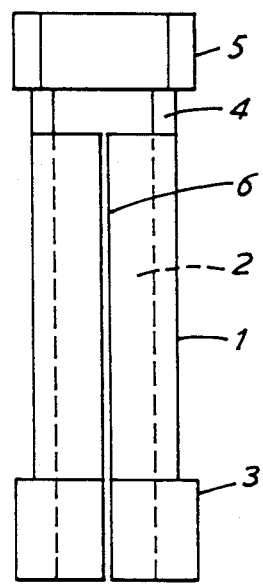
FIG. 1 is a front elevation of the device.
Figure 2:
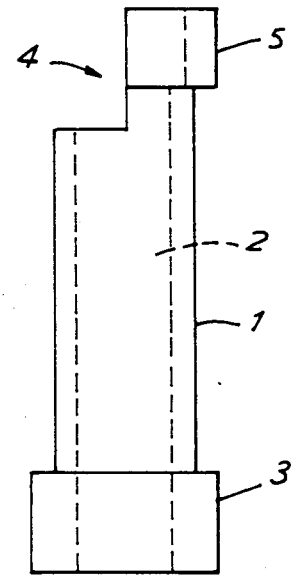
FIG. 2 is a side elevation of the device shown in FIG. 1.

The device, which has the shape of a sleeve, comprises a body 1 substantially in the form of a cylindrical tube with an axial bore 2. The body 1 has at one end an outer annular collar 3 and at the other end is axially/radially cut out so that it has a semi-tubular end 4 provided with a semi-annular collar 5. The body 1 and the collar 3 are provided with an axial slit 6 extending between the outer and inner surfaces of the elements 1 and 3.

Preferably, the material of the vial sleeve is poly-tetra-fluoro-ethylene (PTFE), though other suitable materials such as other plastics, glass, wood, metal, may also be used.

The bore of the vial sleeve may be closed at one end (FIG. 5).

Advantageously, the vials have a cylindrical collar of slightly greater diameter than their cylindrical body primarily to provide means for receiving a crimped-on cap to seal the vial and to ensure the centering of the vial within the sleeve.

The support sleeve has a height of about 32 mm, an outside diameter of about 12 mm and an inside diameter of about 5.8 mm. A typical preferred vial of borosilicate glass with a convex end portion has a length of 32 mm, an outside diameter of 5.6 mm and a collar of 7 mm diameter, thus providing a firm and positive fit within a locating and supporting device. A vial of these dimensions would have a liquid capacity of approximately 0.3 ml.

The vials of the present invention may also be used in certain other commercially available chromatographic autosamplers.

The axial slit 6 allows the vial to be gripped securely, preventing the vial from following after the needle when it is extracted. This is essential in the case of the Hewlett-Packard 1090A liquid chromatographic autosampler. The sleeve must also have an indentation, or neck extending from about 4 mm from the top of the sleeve to within about 10 mm from the bottom. This essential for the GC autosampler 7673A model to enable the robot arm claw to lift the sleeve containing the vial from the carousel, position it in the autosampler turret, and replace it in the carousel after sample extraction.

Referring to FIG. 3 of the drawings, a conventional autosampler 10 includes a carrier 14 located at a sampling station 15 and including a plurality of large openings 16 which normally receive conventional large outer diameter vials. Conventional means 18 move the carrier 14 to present each opening 16 below and in alignment with an aspirator needle or probe 17 (FIGS. 3 and 4) which is part of conventional overall means 20 which moves the probe 17 a predetermined distance from the retracted position (FIG. 4) downwardly toward an extended position (not shown).

When conventional large outer diameter vials (not shown) are carried by the openings 16, the probe 17 can descend into a liquid (not shown) therein and withdraw the same. This liquid is then subsequently conventionally tested by the autosampler 10.

If a liquid in such a large outer diameter vial is at a height below that of the tip of the probe 17 when the probe 17 is in its lowest position, the liquid cannot be withdrawn. Accordingly, in such case the conventional large outer diameter vial is not utilized and instead the precision vial locating and supporting device or sleeve 4 (FIG. 4) is provided. The sleeve 4 has been described heretofore, but also includes an exterior diameter or surface ES which corresponds or matches a diameter D of each opening 16 of the carrier 14. The sleeve 4 also includes a smaller cylindrical interior diameter or surface IS (FIG. 4) in which is located a small outer diameter vial V whose height and volume are measurably smaller than that of a conventional large outer diameter vial. Thus the liquid in the smaller volume vial V can be reached and aspirated by the probe 17 when the latter is in its lowermost position, and once aspirated or withdrawn, the same can be tested automatically and conventionally by the conventional autosampler 10.

I claim:

1. A precision locating and supporting device for accommodating a small outer diameter vial in a larger diameter opening of a variety of different autosamplers and which controls the depth of insertion of autosampler extraction means comprising a sleeve, means defined by an exterior surface of said sleeve for accurately fitting the sleeve in a large diameter opening of an autosampler, means defined by an interior surface of said sleeve for accurately fitting therein a small outer diameter vial whereby an otherwise incompatible small outer diameter vial and larger diameter opening autosampler are rendered compatible, said sleeve including a tubular body having at one end an annular collar and at an opposite end a cut-out defining a semi-tubular end provided with a semi-annular column, and an axial slit extending along the body and collar.

2. A precision locating and supporting device for accommodating a small outer diameter vial in a larger diameter opening of a variety of different autosamplers and which controls the depth of insertion of autosampler extraction means comprising a sleeve, means defined by an exterior surface of said sleeve for accurately fitting the sleeve in a large diameter opening of an autosampler, means defined by an interior surface of said sleeve for accurately fitting therein a small outer diameter vial whereby an otherwise incompatible small outer diameter vial and larger diameter opening autosampler are rendered compatible, said interior surface being an axial bore in which the ratio of the height of the sleeve to outside diameter is in the range of 1.5 to 4.5, the ratio of said outside diameter to said inside diameter is in the range of 1.5 to 2.75, said sleeve being a tubular body having at one end an annular collar and at an opposite end a cut-off defining a semi-tubular end provided with a semi-annular collar and an axial slit extending along the body and collar.

3. A precision locating and supporting device for accommodating a small outer diameter vial in a larger diameter opening of a variety of different autosamplers and which controls the depth of insertion of autosampler extraction means comprising a sleeve, means defined by an exterior surface of said sleeve for accurately fitting the sleeve in a large diameter opening of an autosampler, means defined by an interior surface of said sleeve for accurately fitting therein a small outer diameter vial whereby an otherwise incompatible small outer diameter vial and larger diameter opening autosampler are rendered compatible, said interior surface defines a bore closed at one end, said sleeve being a tubular body having at one end an annular collar and at an opposite end a cut-off defining a semi-tubular end provided with a semi-annular column, and an axial slit extending along the body and collar.

4. A precision locating and supporting device for accommodating a small outer diameter vial in a larger diameter opening of a variety of different autosamplers and which controls the depth of insertion of autosampler extraction means comprising a sleeve, means defined by an exterior surface of said sleeve for accurately fitting the sleeve in a large diameter opening of an autosampler, means defined by an interior surface of said sleeve for accurately fitting therein a small outer diameter vial whereby an otherwise incompatible small outer diameter vial and larger diameter opening autosampler are rendered compatible, said sleeve including a tubular body having at one end an annular collar and at an opposite end a cut-out defining a semi-tubular end provided with a semi-annular column, an axial slit extending along the body and collar, and a vial fitted in said tubular body.

* * * * *